(12) United States Patent
Cadwell

(10) Patent No.: US 6,805,668 B1
(45) Date of Patent: Oct. 19, 2004

(54) SYSTEM AND METHOD FOR PROCESSING PATIENT POLYSOMNOGRAPH DATA UTILIZING MULTIPLE NEURAL NETWORK PROCESSING

(75) Inventor: John A. Cadwell, Richland, WA (US)

(73) Assignee: Cadwell Industries, Inc., Kennewick, WA (US)

( * ) Notice: Subject to any disclaimer, the term of this patent is extended or adjusted under 35 U.S.C. 154(b) by 292 days.

(21) Appl. No.: 10/184,100

(22) Filed: Jun. 26, 2002

Related U.S. Application Data

(60) Provisional application No. 60/301,257, filed on Jun. 26, 2001.

(51) Int. Cl.[7] ............................. A61B 5/04; G06F 15/18
(52) U.S. Cl. ...................... 600/300; 600/529; 600/544; 128/925; 706/924
(58) Field of Search ............................ 600/300–301, 600/544–545, 529; 128/920, 925; 706/924

(56) References Cited

U.S. PATENT DOCUMENTS

| | | |
|---|---|---|
| 4,579,125 A | 4/1986 | Strobl et al. |
| 4,776,345 A | 10/1988 | Cohen et al. |
| 5,299,118 A | 3/1994 | Martens et al. |
| 5,732,696 A | 3/1998 | Rapoport et al. |
| 5,813,993 A | 9/1998 | Kaplan et al. |
| 5,953,713 A | 9/1999 | Behbehani et al. |
| RE36,450 E | 12/1999 | Musha |
| 5,999,846 A * | 12/1999 | Pardey et al. ............... 600/544 |
| 6,070,098 A * | 5/2000 | Moore-Ede et al. ........ 600/300 |
| 6,083,173 A | 7/2000 | Grant et al. |

* cited by examiner

Primary Examiner—Mary Beth Jones
Assistant Examiner—Michael Astorino
(74) Attorney, Agent, or Firm—Christensen O'Connor Johnson Kindness PLLC

(57) ABSTRACT

A system and method for processing patient polysomnograph data are provided. An abstractor obtains raw patient polysomnograph data and generates a subset of the data to include selected factors, including data clusters. The subset of the patient polysomnograph data is transferred to two or more neural networks that process the data and generate sleep classification data. An integrator obtains the sleep classification data from the two or more neural networks by integrating the sleep classification data from each neural network. A cumulative sleep stage score is generated including confidence values and accuracy estimations for review.

30 Claims, 5 Drawing Sheets

SYSTEM AND METHOD FOR PROCESSING PATIENT POLYSOMNOGRAPH DATA UTILIZING MULTIPLE NEURAL NETWORK PROCESSING

CROSS-REFERENCE TO RELATED APPLICATION

This application claims the benefit of U.S. Provisional Patent Application No. 60/301,257, filed Jun. 26, 2001. The above-noted application is incorporated herein by reference in its entirety.

FIELD OF THE INVENTION

In general, the present invention relates to monitoring patient polysomnograph data, and more specifically, to a system and method for scoring patient polysomnograph data and for providing sleep stage score feedback.

BACKGROUND OF THE INVENTION

Sleep disorders are medical problems that can cause debilitation and can be life threatening to an individual. To diagnose sleep disorders, standard practice in clinical research sleep laboratories includes the collection of physiological signals from sleeping patients. The physiological signals can include respiratory activity, blood oxygenation, brain activity, electrocardiogram (EKG), body position, leg and chin movement, etc. The data gathered from these observations can be recorded on paper or electronically for analysis. For example, a typical analysis includes examining six to eight hours of patient data in discrete time periods, such as twenty or thirty seconds, to identify key physiological factors in classifying the sleep stage of an individual.

Conventionally, a standard set of rules defined by Rechtschaffen and Kales is used by trained technicians to assign one of several unique scores, or sleep stages, to the period of time being analyzed. The sleep stages include awake, non-REM stages 1, 2, 3, and 4, and REM. Although the Rechtschaffen and Kales rules are well-defined and standardized in the relative sleep analysis industry, a typical analysis of a sleeping patient gives rise to often conflicting criteria that either satisfies more than one sleep stage, or that conflicts between two sleep stages. Accordingly, a trained technician often requires one to two hours of analysis to make a sleep stage determination. Moreover, the trained technician subjectively determines in which of the sleep stages the patient data is best classified.

In an attempt to automate sleep score analysis, some conventional computer systems have attempted to apply the Rechtschaffen and Kales rules in terms of a system implementing fixed logic, often termed "if, then" programming, for analysis. For example, the computer system would analyze the data by determining whether certain key physiological elements were present, the result of which would direct the computer system to a predetermined sleep stage score. Conventional rules-based systems can become deficient in analyzing the sleep stage of a patient, if the patient data includes conflicting factors under the Rechtschaffen and Kales scale. For example, if the system logic was created such that the presence of one factor results in the determination of a first sleep stage score, while the presence of a second factor results in the determination of a second sleep stage score, the presence of both factors in the patient data would cause the system to eliminate one of the sleep stages depending on the order in which the patient data was processed, or to otherwise not properly process the data.

A rules-based sleep processing system may be further deficient because the fixed logic is typically nonmodifiable. Because a trained technician often makes subjective decisions in processing patient data, the fixed logic also includes at least some subjective decisions inputted by the programmer into the computer system. If a user does not agree with one or more of the subjective decisions, a correction generally requires reprogramming, thereby increasing the cost of the processing system.

Another approach to utilizing computer systems to classify sleep stage scores involves generating a sleep score by utilizing a trained neural network. One skilled in the relevant art will appreciate that as applied to a system for determining a sleep stage score, a neural network system includes a plurality of inputs for accepting the patient data. Each of the inputs is processed by the neural network according to an assigned weight for each particular input. To train the neural network, the weights are adjusted after processing sample data inputs with a desired outcome. By utilizing training processes, such as backward propagation, the neural network can be trained so that the neural network will eventually generate sleep stage score output that mimics the sample data.

The use of neural networks to process patient sleep data generally facilitates the processing patient data that can include conflicting factors to achieve a patient sleep stage score. However, because a neural network relies on training from a sample set, a single neural network does not take into account differences in subjective decisions that may be arrived by two or more trained technicians. Accordingly, trained neural networks are often described as taking on the personality of the trained technician that generated the sample data. However, unlike a trained technician that is capable of providing information as, to why certain factors were considered or why a specific sleep stage score was selected, a system utilizing a single neural network can become deficient in that there is very little information regarding why the neural network generated a given result. For example, the conventional trained neural network does not output what factors were relied upon in calculating the sleep stage score. Additionally, the conventional trained neural network processing system does not indicate confidence values in how likely the calculated sleep stage score is accurate. Thus, a person, such as a trained technician, attempting to review the neural network's determination has no basis for supporting the outcome without a complete independent review.

Neural networks become further deficient in the event the patient data includes too many factors to consider. One skilled in the relevant art will appreciate that patient polysomnograph data may yield a great deal of data (e.g., more than 6,000 data points) that consumes a majority of computer processing resources. Accordingly, a neural network can abstract data by selecting more important factors within the patient data. Conventional neural networks either do not provide data abstraction, or the abstraction is not adequate, thus either consumes processing resources and/or reduces the efficiency of the neural network.

Thus, there is a need for a system and method for processing patient polysomnograph data that can automate a sleep stage score determination and that provides feedback data for review.

SUMMARY OF THE INVENTION

A system and method for processing patient polysomnograph data are provided. An abstractor obtains raw patient polysomnograph data and generates a subset of the data to include selected factors, including data clusters. The subset of the patient polysomnograph data is transferred to two or more neural networks that process the data and generate a sleep classification data. An integrator obtains the sleep classification data from the two or more neural networks by integrating the sleep classification data from each neural network. A cumulative sleep stage score is generated including confidence values and accuracy estimations for review.

In accordance with an aspect of the present invention, a system for processing patient polysomnograph data is provided. The system includes two or more neural networks operable to obtain the patient polysomnograph data and to generate a sleep classification data. The system also includes an interpreter operable to obtain the sleep classification data generated by the two or mote neural networks and to generate a cumulative sleep stage score.

In accordance with another aspect of the present invention, a method for processing patient polysomnograph data is provided. In accordance with the method, a processing system obtains the patient polysomnograph data and obtains sleep classification data corresponding to the patient polysomnograph data from a first neural network. The processing system obtains sleep classification data corresponding to the patient polysomnograph data from a second neural network and integrates the sleep classification data from the first and second neural networks to generate a cumulative sleep stage score.

In accordance with a further aspect of the present invention, a system for processing patient polysomnograph data is provided. The system includes an abstractor operable to obtain patient polysomnograph data and generate a subset of patient polysomnograph data. The system also includes two or more neural networks operable to obtain the subset of patient polysomnograph data and generate a sleep classification data. The system further includes an interpreter operable to obtain the sleep classification data generated by the two or more neural networks and to generate a cumulative sleep stage score, the cumulative sleep stage score including confidence and accuracy values.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention is embodied as a system and method for processing patient polysomnograph data. More specifically, the present invention is embodied as a system and method utilizing multiple neural networks to process patient polysomnograph data in which a resulting calculated sleep stage score can include confidence and accuracy data. One skilled in the relevant art will appreciate that the disclosed embodiments are illustrative, and should not be construed as limiting.

Figure 1:
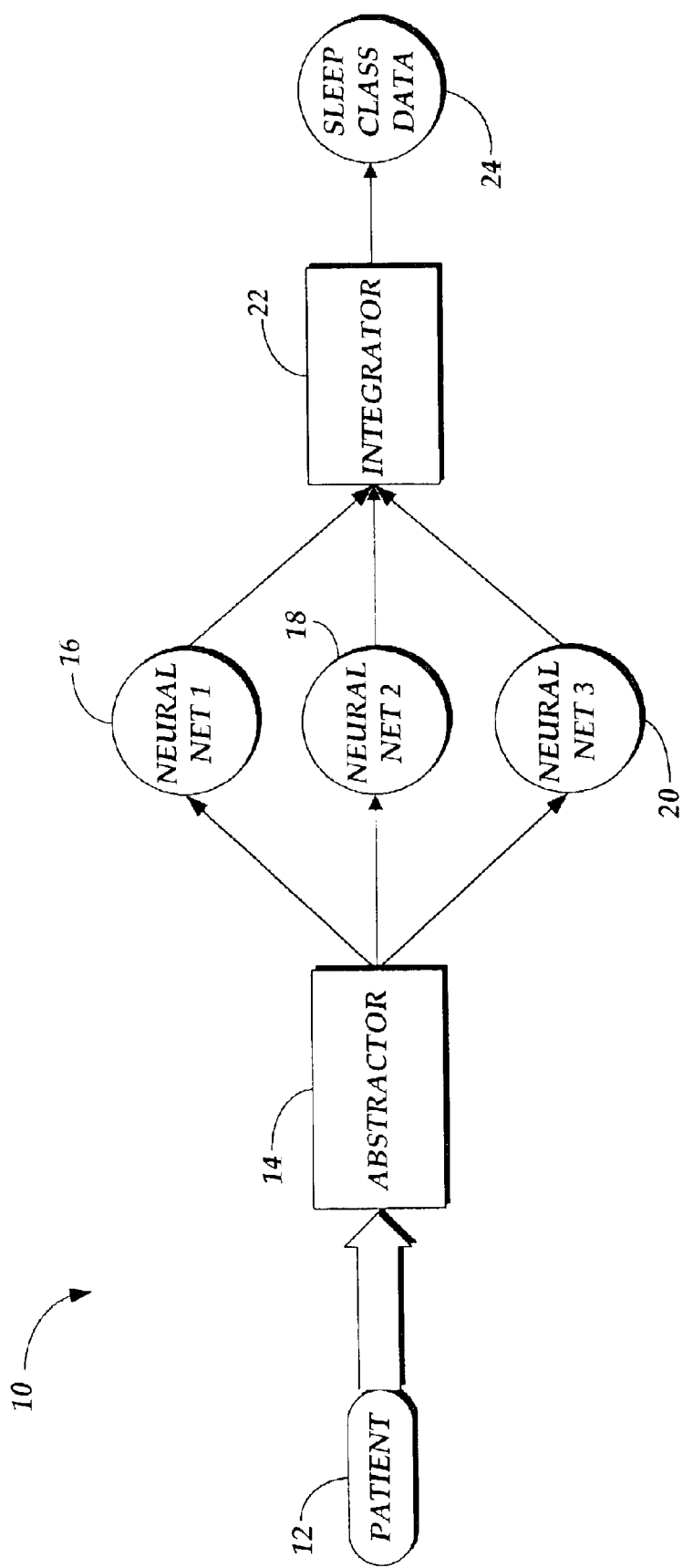
FIG. 1 is a block diagram illustrative of multiple neural network patient data processing system in accordance with the present invention.

FIG. 1 is a block diagram illustrative of a multiple neural network processing system 10 in accordance with the present invention. The processing system 10 includes a patient data gathering system 12 that is operable to obtain and transmit patient data to the system. The patient data gathering system 12 can include one or more devices operable to obtain the patient data from measurement leads connected to a patient. The patient data may be grouped by the patient data gathering system 12, or may be directly transmitted to the processing system 10. The processing system 10 also includes an abstractor 14 operable to obtain the raw patient data and generate a set of physiological data factors to be processed by the system 10. In an illustrative embodiment of the present inventor, the abstractor 14 obtains raw patient data and generates a reduced set of physiological factors that include data clusters of one or more factors. A more detailed description of the abstractor 14 will be explained below.

In an illustrative embodiment of the present invention, the processing system 10 includes two or more neural networks utilized to concurrently process the abstracted patient data. As illustrated in FIG. 1, the processing system 10 includes three neural networks 16, 18, 20 that concurrently receive identical sets of patient data input from the abstractor 14 and which each generates a set of outputs in the form of a sleep stage score. One skilled in the relevant art will appreciate that the number of neural networks within the system may be modified and that the configuration for the multiple neural networks may also vary. For example, the neural networks 16, 18, 20 may be configured in series with one another.

The processing system 10 includes an integrator 22 operable to obtain the set of outputs from each neural network 16, 18, 20 and to generate sleep classification data 24. As will be explained in greater detail below, the sleep classification data 24 can include a calculated sleep stage score in accordance with industry standards such as the Rechtschaffen and Kales rules. The sleep classification data 24 can also include confidence values that compare a numerical confidence value in a selected sleep stage score with numerical confidence values for non-selected sleep stage scores. The sleep classification data 24 can further include accuracy data to provide details, such as a ranked list of patient data factors primarily relied upon, detailing why a specific sleep stage score was selected.

Figure 2:
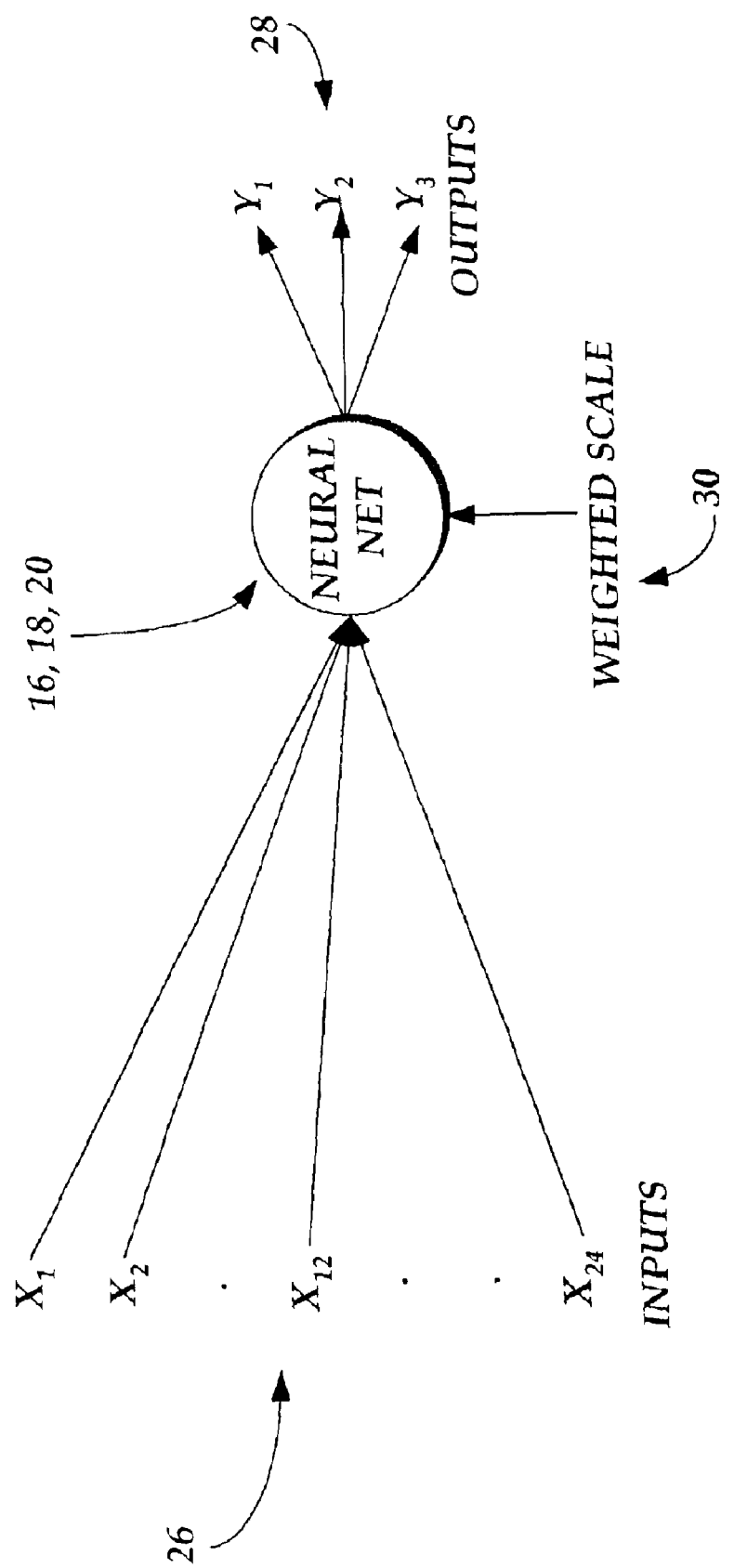
FIG. 2 is a block diagram illustrative of a neural network for processing patient data in accordance with the present invention.

Referring now to FIG. 2, an illustrative description of a feed-forward neural network utilized in accordance with the present invention will be described. One skilled in the relevant art will appreciate that neural networks may have additional or alternative components than those described in FIG. 2, and that the description is solely for illustrative purposes. For example, the feed-forward neural network may be implemented as a single layer or a multiple layer neural network. Additionally, the neural network may also be implemented as a recurrent neural network. A more detailed description of neural networks is described in Simon Haykin, *Neural Networks A Comprehensive Foundation*, 1994, the disclosure of which is incorporated by referenced herein.

As illustrated in FIG. 2, an artificial neural network is constructed such that it receives a number of inputs 26, that are concurrently processed to generate a set of outputs 28. In an illustrative embodiment of the present invention, the neural networks obtain a series of 24 patient polysomnograph data inputs 26 to generate at least 3 outputs 28 relating to a calculated sleep stage score. As utilized in the present invention, each neural network 16, 18, 20 is configured with a series of 24 weight values 30 that correspond to each of the patient data inputs 26 provided to the neural network and that are utilized to generate the 3 outputs 28.

Figure 3:
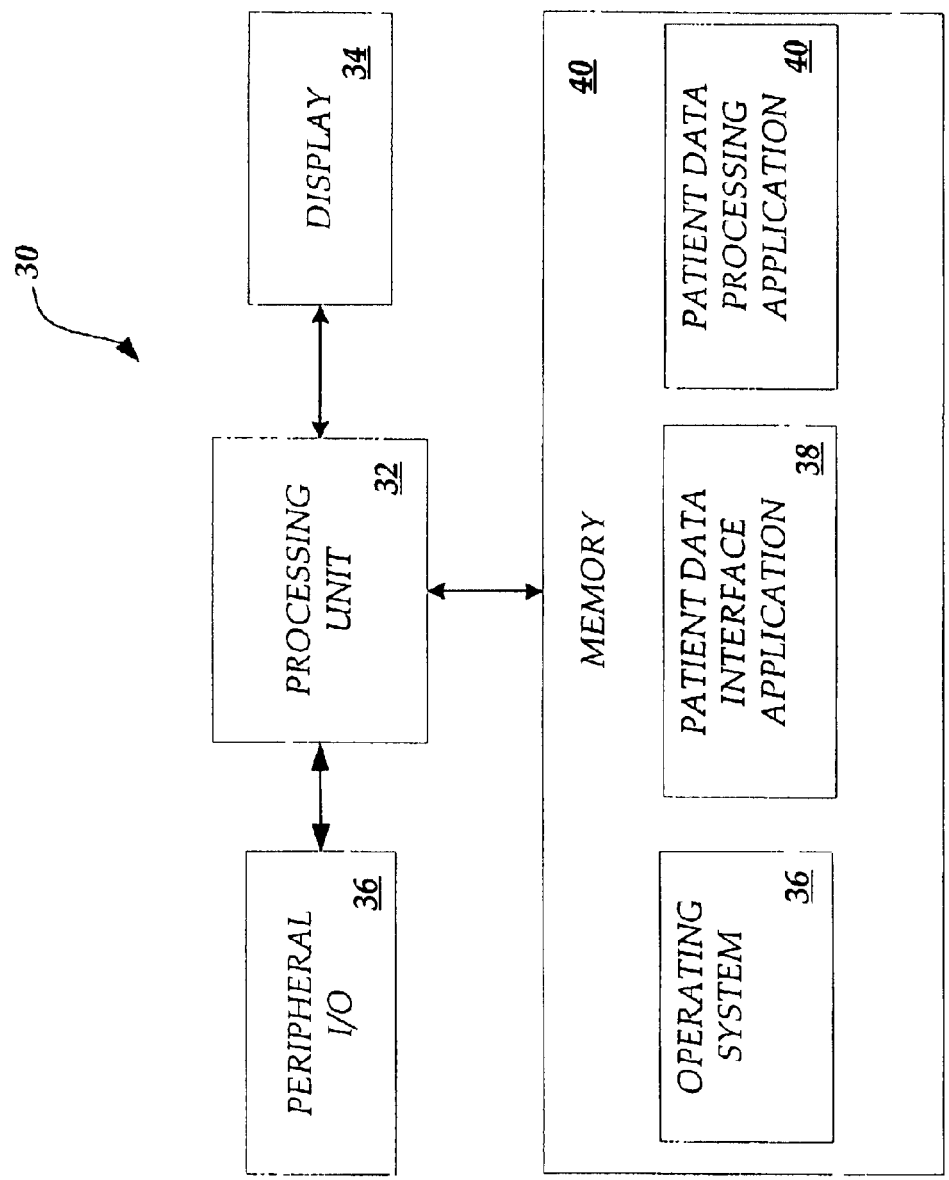
FIG. 3 is a block diagram depicting an illustrative architecture for a patient data processing computing device in accordance with the present invention.

FIG. 3 depicts several of the key components of an illustrative computing device 26 operable to implement a neural network, such as neural networks 16, 18, 20. Those of ordinary skill in the art will appreciate that the neural network computing device 26 includes many more components than those shown in FIG. 3. However, it is not necessary that all of these generally conventional components be shown in order to disclose an illustrative embodiment of the invention.

As shown in FIG. 3, neural network computing device 26 includes a processing unit 28, a display 30, a peripheral input/output 32 and a memory 34. As applied to the present invention, the peripheral input/output 32 may accept inputs from a variety of patient polysomnograph monitoring devices connected to the neural network computing device 26 including, but not limited to, electroencephalograph ("EEG") devices, motion detecting device, temperature detection devices, video recording devices, and the like. One skilled in the relevant art will appreciate that the peripheral input/output 32 may also accept inputs to one or more processing devices that are connected directly to the patient polysomnograph monitoring devices. In an illustrative embodiment of the present invention, the neural network computing device 26 may also include additional components such as modems or network interfaces for communication with other neural network computing devices 26, the processing system 10 and/or other devices associated with processing patient polysomnograph data.

The memory 34 generally comprises a random access memory ("RAM"), a read-only memory ("ROM") and a permanent mass storage device, such as a disk drive. The memory 34 stores an operating system 36 for controlling the operation of the neural network computing device 26. In an actual embodiment of the present invention, the operating system 36 provides a graphical operating environment, such as Microsoft Corporation's WINDOWS® graphical operating system in which activated application programs are represented as one or more graphical application windows with a display visible to the user. The Memory 34 also stores program code for obtaining and processing the patient polysomnograph data ("patient data"). Specifically, the memory 34 includes a patient data interface application 38 for obtaining patient data and a patient data processing application 40 for generating sleep classification data formed in accordance with the present invention. It will be appreciated that memory components may be stored on a computer-readable medium, such as a floppy, CD-ROM, DVD-ROM drive, or other network drive and loaded into the memory 34 of the neural network computing device 26 using a drive mechanism associated with the computer-readable medium.

The memory 34, display 30, and peripheral input/output 32 are all connected to the processing unit 28 via one or more buses. As will be generally understood by those skilled in the are and others, other peripherals may also be connected to the processing unit 28 in a similar manner. Moreover, although the neural network computing device 26 has been described with relation to two application components for implementing the measurement and quantification process of the present invention, incorporation of an alternative number of components is within the scope of the present invention.

In an illustrative embodiment of the present invention, to configure a neural network 16, 18, 20, each of the weight values 30 is initialized with random values for processing. The neural network is then given a training set in which a desired output is known for a given set of inputs. As the neural network processes the inputs based on the current weight values 30, the actual output from the neural network is compared to the desired output of the sample set. If the outputs are the same, or within a margin of error, the weight values 30 are not adjusted. Alternatively, if the difference between the outputs is not satisfactory, the weight values 30 may be adjusted. Accordingly, the training process may be repeated until the weight values 30 are adjusted to satisfaction of a trainer.

The training of a neural network in which the output does not affect its input, known as a feed-forward neural network. In an illustrative embodiment of the present invention, a back propagation learning procedure is utilized to train feed-forward network. One skilled in the relevant art will appreciate that a back propagation learning procedure is based on a sum of the squared error for each node associated with the neural network. Equation (1) models back-propagation error evaluation as follows:

$$E(i) = 1/2 \sum_{i \in C} (p_t - t_t)^2 \qquad (1)$$

As illustrated in Equation (1) the total error, E, is equal to the sum of the square of the desired output, $p_t$, minus the actual output, $t_t$, for each node in the neural network where C is the total number of nodes in the neural network.

In accordance with a back-propagation learning procedure, the various weight values 30 are adjusted after processing each set of test data to minimize the mean squared error, E. Equation (2) illustrates a mathematical formula for adjusting each weight value 30 as follows:

$$\Delta w_{ji}(n) = \eta \delta_j(n) Y_i(n)$$

As illustrated in Equation (2), the change in weight value $\Delta w_{ji}(n)$, for each training iteration, n, is equal to the product of the learning rate parameter, $\eta$, a local gradient of the output, $\delta_j(n)$, and the output signal at node, Yi(n). One skilled in the relevant art will appreciate that Equation (2) estimates a true change that would occur by modifying weight values, $w_{ji}(n)$. A more detailed analysis of the squared error minimization is described in Simon Haykin, *Neural Networks A Comprehensive Foundation*, referenced above.

In an illustrative embodiment of the present invention, a graphical interface may be provided by the processing system to graphically illustrate the total error, E, resulting from the processing of the training set. In an illustrative embodiment of the present invention, the total error may be graphically illustrated in terms of a bar or line graph, in which the bar/line is equal to the calculated total error. As the error is reduced, the graphical interface may display the resulting graph in terms of a horizontal line or bar within a satisfactory range. One skilled in the relevant art will appreciate that alternative training methods or more complex training methods may be utilized in accordance with more complex neural networks, or different neural networks, and are considered to be within the scope of the present invention. Moreover, the alternative graphical user interfaces may also be utilized in accordance with the present invention.

As described above, conventionally, neural networks may be trained using a single set of data inputs in which a desired output, or group of outputs, is known. However, one skilled in the relevant art will appreciate the neural network weight values 30 are initialized with random values, neural networks trained utilizing a back-propagation learning procedure may arrive at the same sleep stage score with different weight values 30. Thus, in certain situations, weight value adjustments from a single training set may appear to yield desirable results, but could lead to varied results in subsequent use. More specifically, the weight value 30 adjustments may be based on one or more factors that overly influenced the outputs of the neural network. For example, assume that a training set causes a neural network to determine a sleep stage score based on the unique adjustment to a key patient data factor. In subsequent uses, if patient data does not include the factor, or the factor is not as prominent, the resulting sleep stage score may be inconclusive, or otherwise incorrect.

In accordance with a training aspect of the present invention, multiple trained sets for each sleep stage score classification are utilized to train a neural network 16, 18, 20. Each trained set includes different factors that should result in an output of the same sleep stage score. If the neural network outputs the same sleep stage score for the multiple each training sets, the accuracy is more likely correct. If the neural network does not output the same sleep stage score, the accuracy of the neural network may be questioned. In the event the accuracy of the training is questioned, the weight values 30 of the neural network 16, 18, 20 may be reinitialized and the training process may be repeated.

Figure 4:
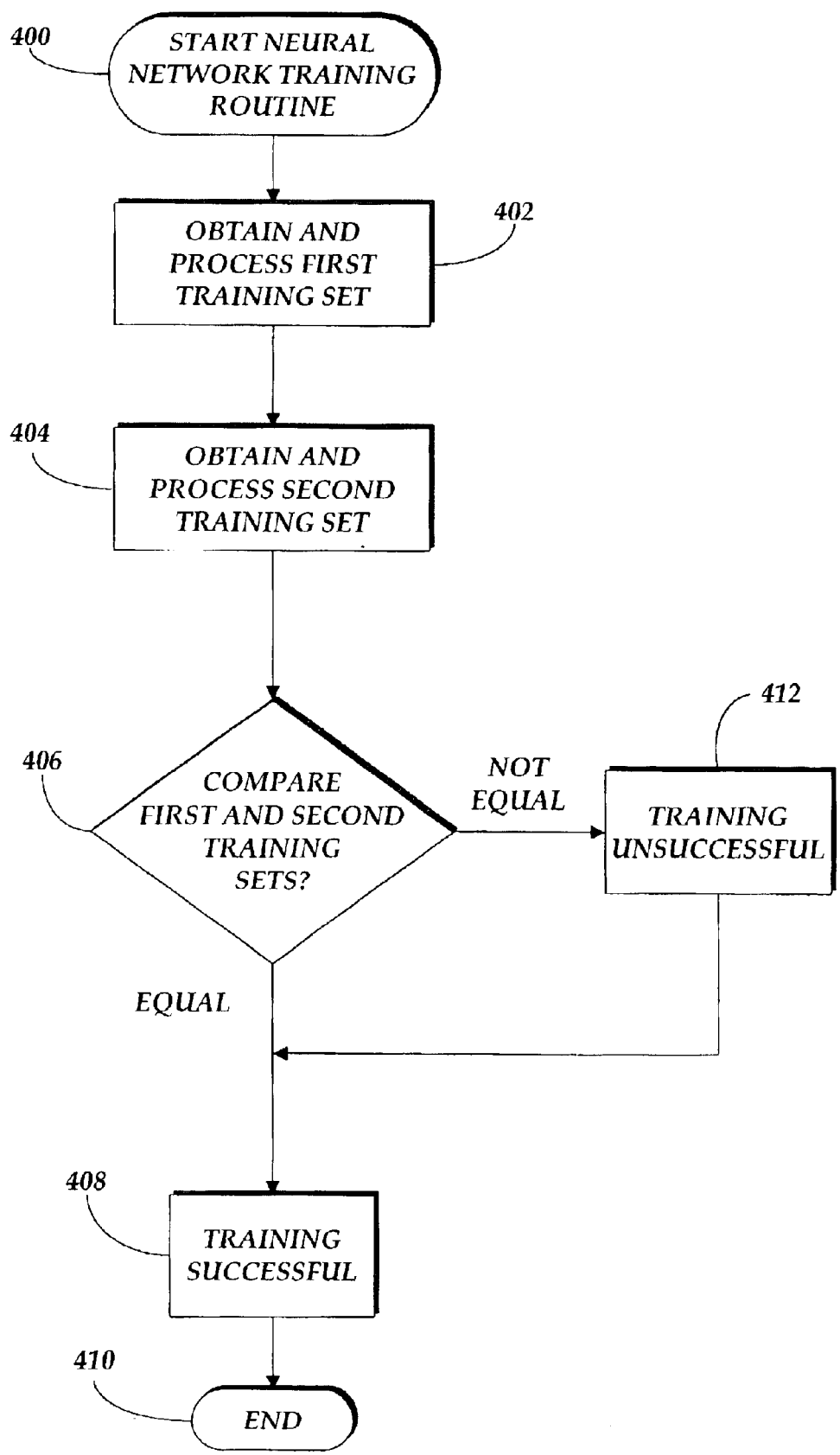
FIG. 4 is a flow diagram illustrative of a multiple set neural network training routine in accordance with the present invention.

FIG. 4 is a flow diagram illustrative of a multiple set neural network training routine 400 in accordance with the present invention. At block 402, a first set of training inputs is obtained and processed to generate a set of outputs. In an illustrative embodiment of the present invention, at block 404, a second set of training inputs is obtained and processed to generate a second set of outputs. In an illustrative embodiment of the present invention, each training set is configured such that the known output, or set of outputs, should result in the determination of the same sleep stage score based on different patient data inputs. At decision block 406, a test is done to determine whether the first and second sets of outputs are the same. If the outputs are the same at block 408, the multiple training set processing is considered successful, and the routine 400 terminates at block 410. Alternatively, if the training sets are not at the same level at decision block 406, at block 412, the multiple training set processing is not considered successful, and routine 400 terminates at block 410.

In an illustrative embodiment of the present invention, the utilization of multiple training sets allows for a more robust testing of the neural network processing abilities. More specifically, because the neural network is expected to generate the same sleep stage score for each training set, a single correct calculation will not be adequate because this indicates that the neural network may only have a limited processing and more may generate incorrect scores for a set of inputs. The multiple training set is repeated for each stage the neural network may calculate. Additionally, although the training sets are illustrated in FIG. 4, one skilled in the relevant art will appreciate that more than two training sets may be used on each sleep stage score for the training.

Figure 5:
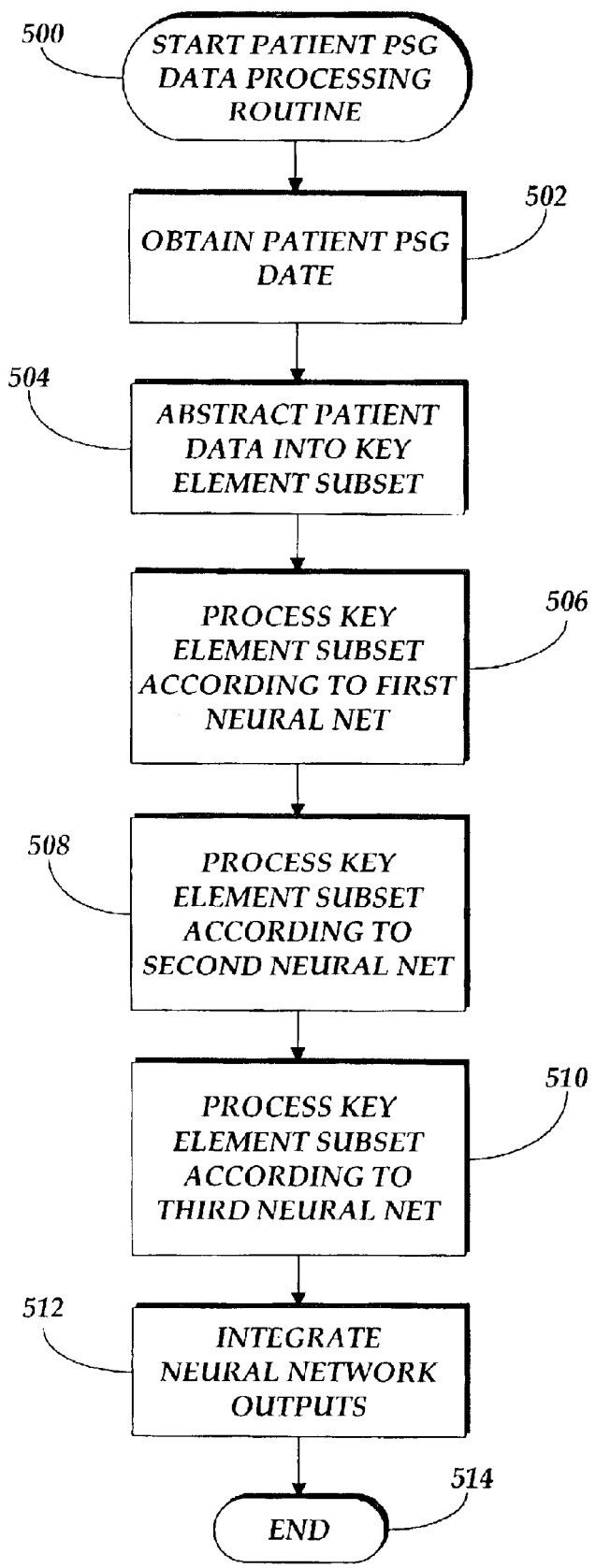
FIG. 5 is a flow diagram of a patient data processing routine in accordance with the present invention.

Referring now to FIG. 5, a flow diagram of a patient data processing routine 500 implemented by the multiple neural network processing system 10 will be described in accordance with the present invention. At block 502, the processing system 10 obtains patient polysomnograph data from the patient data gathering system 12. At block 504, the abstractor 14 abstracts the patient polysomnograph data into key physiological element subset. In an illustrative embodiment of the present invention, the abstractor 14 abstracts the patient data into a subset of twenty-four key physiological elements. The key physiological elements may be elements utilized in the standard industry, as well as elements specified by particular individuals. In an actual embodiment of the present invention, the key physiological elements include a fast fourier transform for power in a delta band, the fast fourier transform for power in theta band, a fast fourier transform for power in an alpha band, a ratio of alpha band power to delta band power, a total power in the beta, alpha, delta, and theta band, a number of alpha wave segments, a total area of alpha wave segments, a percentage of pages comprised of K-complexes, a number of K-complexes per page, a percent of a page comprised of K-complexes, a number of spindles per page, a total area of spindle wave segments, a percentage of pages comprised of spindles, a number of position changes per page, a number of eye movements both in and out of phase per page, a percentage of page with eye movements, a number of REM movements per page, a ratio of eye movements in a first half to a second half of page, a measure of in-phase versus out-of-phase activity, a number of chin movements per page, a total area of chin activity, a percentage of page with chin activity, a ratio of chin activity on a first half versus a second half of a page, and a total area of chin versus EEG noise.

In an illustrative embodiment of the present invention, a portion or all of the key physiological elements may include data clusters of the inputted patient data. One skilled in the relevant art will appreciate that transforming data mathematically by merging multiple clusters of data facilitates processing the data by a neural network. For example, by presenting of ratio of alpha versus delta power, a neural network can analyze high alpha/high delta and low alpha/low delta with a single cluster. Accordingly, clustering data mitigates the number of inputs processed by the neural network, thereby decreasing a drain on processing resources. One skilled in the relevant art will appreciate that additional or alternative data clusters may be included in the present invention.

Additionally, the abstractor 14, may modify the number of key physiological elements included in the present invention.

At block 506, a first neural network 16 processes the subset of key elements from the abstractor 14 according to a first set of weight values 30. At block 508, a second neural network processes the subset key elements according to a second set of weights 30. At block 508, a third neural network processes the subset of key physiological elements according to a third set of weight value values 30.

At block 512, the integrator 22 obtains the outputs from each of the neural networks to generate sleep classification data 24. In an illustrative embodiment of the present invention, the integrator obtains the first output from the first neural network and compares it to the second and third outputs. If all the neural networks are in agreement, the integrator will select sleep classification score. However, if the neural networks are not in agreement, the integrator 22 may either reject the sleep classification score or accept a majority selection, if two or more of the neural networks agree as to a sleep classification score.

In an illustrative embodiment of the present invention, the integrator 22 may also generate or obtain from the neural network confidence values relating to the selection of a sleep stage score. For example, each neural network generates a sleep stage score by selecting one of the six possible sleep stage scores: awake 1, non-REM 1, 2, 3, 4, and REM. The selection is based on a fractional numerical value between 0.0 and 1.0. Typically, the neural network selects the sleep stage score having the highest numerical number. For example, if sleep stage score for non-REM 3 has a value of 0.8, while the remaining values have some numerical value less than that, the neural network selects the sleep stage score 3.

In some cases, the neural network may select a sleep stage score that is relatively close to one or more non-selected sleep stage scores. In accordance with the present invention, to transmit a confidence in a selected sleep stage score, a confidence value is calculated. More specifically, the confidence value may be calculated as the numerical value for a selected stage divided by the sum of numerical values for all the states. Equation 4 illustrates the confidence value calculation as $$\frac{Value_{Selected}}{\sum_{i=0}^{6} Value_i} = \text{Confidence Value} \quad (4)$$

With reference to the previous example, assume that the neural network calculates that a numerical value for the possibility for a wake state as 0.0, that the value for the first stage I of a non-REM sleep stage is 0.1; stage 2 is 0.2; stage 4 is zero 0.0; and REM is 0.0. Applying Equation 4 to calculate a confidence value, the numerical value for the selected, stage 3, is divided by the sum of all numerical values for all six stages. Equation 5 illustrates the application:

$$0.8/0.1+0.2+0.8)=0.72 \quad (5)$$

Accordingly, the confidence value for the selection of stage 3 is 0.72, which indicates a high confidence value for the selection.

In comparison, assume that for a different subset of data the numerical value for stage 3 is 0.3, while the stage 1 and stage 2 scores are 0.2 and 0.25. An application of the confidence value, illustrated by Equation 6:

$$0.3/(0.2+0.25+0.3)=0.4 \quad (6)$$

As illustrated in Equation 6, the confidence value for the second subset of data yields a lower confidence value. Accordingly, by examining the confidence value, a trained technician may quickly determine a relative confidence in the selected sleep stage score.

In an illustrative embodiment of the present invention, the sleep classification data 24 may also include accuracy data to facilitate review by a trained technician. More specifically, the integrator may obtain or generate a rank list of the criteria relied upon in determining the sleep stage score. For example, if the neural network processing system 12 relied upon a percentage of pages comprising spindles and the number of eye movements both in and out of phase per page in selecting a certain sleep stage score, the rank list would indicate those factors in the order of importance. Accordingly, a trained technician could review the ranked list to quickly determine whether the selected factors are sufficient to be relied upon to merit the determination of the sleep stage score. Moreover, in conjunction with the conference value calculation, the ranked list for accuracy could determine not only how likely the sleep stage score is correct, but also the primary reason why that sleep stage score is proper.

In an illustrative embodiment of the present invention, the multiple neural network processing system further allows for the application of multiple personality neural networks in determining a sleep stage score. More specifically, the multiple neural network processing system may be configured such that a user may select certain personality traits for one or more of the neural networks. As mentioned previously, the determination of a sleep stage score includes a substantial portion of subjective determinations of the criteria. Because a neural network is trained according to a set of data configured by a specific trained person, the neural network incorporates the subjective decisions made by that trained person. Accordingly, the neural network is said to take on the personality of the trained person.

To allow for the application of multiple neural networks, the present invention allows for the storage and retrieval of specifically trained personalities in each of the neural networks. For example, a first neural network may be configured according to a first personality, while the second and third neural networks are configured to different personalities. By allowing multiple personalities to be included, a user can have the patient data analyzed by three sets of training data, without having to adjust the system. Moreover, in the event the user does not agree with the determinations of a specific trained set, a new personality may be created or loaded into the system. For example, a trained personality may be loaded onto a storage medium, such as a CD-Rom, floppy disk, network drive, and be loaded onto a complying device. Moreover, the personality may be transmitted over communication media, such as the Internet, to one or more other devices. Accordingly, the present invention provides flexibility in the processing system 10 without requiring additional programming.

While an illustrative embodiment of the invention has been illustrated and described, it will be appreciated that various changes can be made therein without departing from the spirit and scope of the invention.

What is claimed is:

1. A system for processing a set of patient polysomnograph data, the system comprising:
   two or more distinct neural networks, each neural network obtaining the set of patient polysomnograph data and generating a sleep classification data therefrom; and
   an interpreter obtaining the sleep classification data generated by the two or more neural networks and generating a cumulative sleep stage score.

2. The system as recited in claim 1 further comprising an abstractor operable to obtain the patient polysomnograph data and generate a subset of the patient polysomnograph data.

3. The system as recited in claim 2, wherein the subset of the patient polysomnograph data includes at least 24 factors.

4. The system as recited in claim 3, wherein the factors include a selection from the group consisting of a fast fourier transform in a delta band, a fast fourier transform power in a beta band, fast fourier transform power in an alpha band, a ratio of alpha band power to delta band power, a total power in the delta, alpha and beta band, a number of alpha wave segments, a total area of alpha wave segments, a percentage of pages comprised of K-complexes in the alpha band, a number of K-complexes per page, a percentage of pages comprised of K-complexes in the delta band, a number of spindles per page, a total area of spindle segments, a percentage of pages comprising spindles, a number of position changes per page, a number of eye movements both in and out of phase per page, a percentage of pages with eye movements, a number of REM movements per page, a ratio of eye movements in a first half versus a second half of page, a measure of in-phase versus out-of-phase activity, a number of chin movements per page, a total area of chin activity, a percentage of page with chin activity, a ratio of chin activity in a first half versus a second half per page, and a total area of chin/EEG noise.

5. The system as recited in claim 2, wherein the abstractor is further operable to generate at least one patient data cluster, the patient data cluster including a grouping of two or more patient data factors.

6. The system as recited in claim 5, wherein the patient data cluster includes a ratio of eye movements in a first half versus a second half of a page.

7. The method recited in claim 5, wherein the patient data cluster includes a ratio of chin activity in a first half versus a second half of a page.

8. The system as recited in claim 1, wherein the cumulative sleep stage score is generated by integrating sleep classification data from a first neural network with sleep classification data obtained from a second neural network.

9. The system as recited in claim 1, wherein the interpreter is further operable to generate a confidence value for the cumulative sleep stage score.

10. The system as recited in claim 9, wherein the confidence value is embodied as the quotient of a numerical value corresponding to a selected sleep stage score divided by the sum of numerical values for every possible sleep stage score.

11. The system as recited in claim 1, wherein the interpreter is further operable to generate a ranked list of patient data factors relied upon to generate the cumulative sleep stage score.

12. A method for processing a set of patient polysomnograph data, the method comprising:
   obtaining the patient polysomnograph data;
   obtaining sleep classification data corresponding to the processing of the set of patient polysomnograph data from a first neural network;
   obtaining sleep classification data corresponding to the processing of the set of patient polysomnograph data from a second neural network, wherein the second neural network is distinct from said first neural network;
   integrating the sleep classification data from the first and second neural network to generate a cumulative sleep stage score.

13. The method as recited in claim 12 further comprising abstracting the patient polysomnograph data to generate a subset of the patient polysomnograph data prior to obtaining the sleep stage score from the first and second neural networks.

14. The method as recited in claim 13, wherein the subset of the patient polysomnograph data includes at least 24 factors.

15. The method as recited in claim 12, wherein the factors include a selection from the group consisting of a fast fourier transform in a delta band, a fast fourier transform power in a beta band, fast fourier transform power in an alpha band, a ratio of alpha band power to delta band power, a total power in the delta, alpha and beta band, a number of alpha wave segments, a total area of alpha wave segments, a percentage of pages comprised of K-complexes in the alpha band, a number of K-complexes per page, a percentage of pages comprised of K-complexes in the delta band, a number of spindles per page, a total area of spindle segments, a percentage of pages comprising spindles, a number of position changes per page, a number of eye movements both in and out of phase per page, a percentage of pages with eye movements, a number of REM movements per page, a ratio of eye movements in a first half versus a second half of page, a measure of in-phase versus out-of-phase activity, a number of chin movements per page, a total area of chin activity, a percentage of page with chin activity, a ratio of chin activity in a first half versus a second half per page, and a total area of chin/EEG noise.

16. The method as recited in claim 12 further comprising generating at least one patient data cluster, the patient data cluster including a grouping of two or more patient data factors.

17. The method as recited in claim 16, wherein the patient data clusters includes a ratio of eye movements in a first half versus a second half of a page.

18. The method as recited in claim 16, wherein the patient data cluster includes a ratio of chin activity in a first half versus a second half of a page.

19. The method as recited in claim 12 further comprising generating a confidence value for the cumulative sleep stage score.

20. Method as recited in claim 19, wherein the confidence value is embodied as the quotient of a numerical value corresponding to a sleep stage score divided by the sum of numerical values for each possible sleep stage score.

21. The method as recited in claim 12 further comprising generating a ranked list of patient data factors relied upon to generate the cumulative sleep stage score.

22. A computer-readable medium having computer-implementable instructions for performing the method recited in any one of claims 12–21.

23. A computer system having a processor, an operating environment, and a memory, the computer system operable to perform the method recited in any of claims 12–21.

24. A system for processing patient polysomnograph data, the system comprising:
   an abstractor operable to obtain obtaining patient polysomnograph data and generate generating a subset of patient polysomnograph data;
   two or more distinct neural networks, each neural network operable to obtain obtaining the set of patient polysomnograph data and generate generating a sleep classification data therefrom; and
   an interpreter operable to obtain obtaining the sleep classification data generated by the two or more neural networks and to generate generating a cumulative sleep stage score including confidence and accuracy values.

25. The system as recited in claim 24, wherein the subset of the patient polysomnograph data includes at least 24 factors.

26. The system as recited in claim 24, wherein the factors include a selection from the group consisting of a fast fourier transform in a delta band, a fast fourier transform power in a beta band, fast fourier transform power in an alpha band, a ratio of alpha band power to delta band power, a total power in the delta, alpha and beta band, a number of alpha wave segments, a total area of alpha wave segments, a percentage of pages comprised of K-complexes in the alpha band, a number of K-complexes per page, a percentage of pages comprised of K-complexes in the delta band, a number of spindles per page, a total area of spindle segments, a percentage of pages comprising spindles, a number of position changes per page, a number of eye movements both in and out of phase per page, a percentage of pages with eye movements, a number of REM movements per page, a ratio of eye movements in a first half versus a second half of page, a measure of in-phase versus out-of-phase activity, a number of chin movements per page, a total area of chin activity, a percentage of page with chin activity, a ratio of chin activity in a first half versus a second half per page, and a total area of chin/EEG noise.

27. The system as recited in claim 24, wherein the abstractor is further operable to generate at least one patient data cluster, the patient data cluster including a grouping of two or more patient data factors from the subset of patient polysomnograph data.

28. The system as recited in claim 27, wherein the patient data cluster includes a ratio of eye movements in a first half versus the second half of a page.

29. The system as recited in claim 27, wherein the cumulative sleep stage scores generated by obtaining a sleep stage score from a first neural network and adjusting the sleep stage score by a sleep stage score obtained from a second neural network.

30. The system as recited in claim 24, wherein the confidence value is embodied as a quotient of a numerical value corresponding to a selected sleep stage score divided by the sum of numerical values for every possible sleep stage score.

* * * * *

UNITED STATES PATENT AND TRADEMARK OFFICE
CERTIFICATE OF CORRECTION

PATENT NO.       : 6,805,668 B1                          Page 1 of 2
APPLICATION NO.  : 10/184100
DATED            : October 19, 2004
INVENTOR(S)      : J.A. Cadwell It is certified that error appears in the above-identified patent and that said Letters Patent is hereby corrected as shown below:

| COLUMN | LINE | ERROR |
|---|---|---|
| 10 (Claim 2, line 1) | 49 | "claim 1" should read --claim 1,-- |
| 10 (Claim 4, line 4) | 58 | "band, fast" should read --band, a fast-- |
| 11 (Claim 12, line 11) | 44 | "work;" should read --work; and-- |
| 11 (Claim 13, line 1) | 48 | "claim 12" should read --claim 12,-- |
| 11 (Claim 15, line 4) | 59 | "band, fast" should read --band, a fast-- |
| 12 (Claim 16, line 1) | 10 | "claim 12" should read --claim 12,-- |
| 12 (Claim 17, line 2) | 14 | "data clusters" should read --data cluster-- |
| 12 (Claim 19, line 1) | 20 | "claim 12" should read --claim 12,-- |
| 12 (Claim 20, line 1) | 23 | "20. Method" should read --20. The method-- |
| 12 (Claim 21, line 1) | 27 | "claim 12" should read --claim 12,-- |
| 12 (Claim 23, line 3) | 35 | "any of" should read --any one of-- |
| 12 (Claim 24, line 3) | 38 | delete "operable to obtain" |

UNITED STATES PATENT AND TRADEMARK OFFICE
CERTIFICATE OF CORRECTION

PATENT NO. : 6,805,668 B1
APPLICATION NO. : 10/184100
DATED : October 19, 2004
INVENTOR(S) : J.A. Cadwell It is certified that error appears in the above-identified patent and that said Letters Patent is hereby corrected as shown below:

| COLUMN | LINE | ERROR |
|---|---|---|
| 12 (Claim 24, | 39 line 4) | delete "generate" |
| 12 (Claim 24, | 42 line 7) | delete "operable to obtain" |
| 12 (Claim 24, | 43 line 8) | delete "generate" |
| 12 (Claim 24, | 45 line 10) | delete "operable to obtain" |
| 12 (Claim 24, | 47 line 12) | delete "to generate" |
| 12 (Claim 26, | 55 line 4) | "band, fast" should read --band, a fast-- |
| 14 (Claim 29, | 2 line 2) | "stage scores generated" should read --stage score is generated-- |

Signed and Sealed this

Fifth Day of February, 2008

JON W. DUDAS
*Director of the United States Patent and Trademark Office*